US005232707A

United States Patent [19]

Lokensgard

[11] Patent Number: 5,232,707

[45] Date of Patent: Aug. 3, 1993

[54] SOLVENT EXTRACTION PROCESS

[75] Inventor: David M. Lokensgard, San Jose, Calif.

[73] Assignee: Syntex (U.S.A.) Inc., Palo Alto, Calif.

[21] Appl. No.: 759,803

[22] Filed: Sep. 13, 1991

Related U.S. Application Data

[63] Continuation of Ser. No. 377,648, Jul. 10, 1989, abandoned.

[51] Int. Cl.[5] .......... A61K 9/16

[52] U.S. Cl. .......... 424/490; 424/462; 424/468; 424/497; 264/4.33; 264/4.6; 530/313; 521/56

[58] Field of Search .......... 424/490, 468, 462, 497; 264/4.6, 4.33; 530/313; 521/56

[56] References Cited

U.S. PATENT DOCUMENTS

| | | | |
|---|---|---|---|
| 3,773,919 | 11/1973 | Boswell et al. | 424/19 |
| 3,843,824 | 10/1974 | Roselius et al. | 426/386 |
| 4,234,571 | 11/1980 | Nestor | 530/313 |
| 4,305,838 | 12/1981 | Iwasaki | 252/316 |
| 4,389,330 | 6/1983 | Tice | 427/213.36 |
| 4,675,189 | 6/1987 | Kent | 424/490 |
| 4,777,154 | 10/1988 | Torobin | 521/56 |
| 4,801,577 | 1/1989 | Nestor et al. | 514/15 |
| 4,818,542 | 4/1989 | DeLuca | 424/491 |

FOREIGN PATENT DOCUMENTS

| | | |
|---|---|---|
| 8286745 | 2/1983 | Australia . |
| 3323940 | 1/1985 | Fed. Rep. of Germany . |
| 0258416 | 7/1988 | German Democratic Rep. . |
| 61-035802 | 6/1986 | Japan . |
| 1106468 | 3/1968 | United Kingdom . |
| 2151202 | 7/1985 | United Kingdom . |

*Primary Examiner*—Thurman K. Page
*Assistant Examiner*—W. Benston, Jr.
*Attorney, Agent, or Firm*—William Schmonsees; David A. Lowin; Tom M. Moran

[57] ABSTRACT

There is disclosed a process for the extraction of volatile solvents entrained in a polymer-based pharmaceutical composition designed for sustained release of drug over an extended period of time prepared in microcapsule form wherein the composition comprises at least one hormonally active water-soluble polypeptide in an effective amount greater than a conventional single dose and a biocompatible, bioerodable encapsulating polymer, which process comprises the steps of contacting the composition to a stream of dense gas, that is, pressurized gas and then removing the dense gas, and volatile solvents contained therein, extracted from the pharmaceutical composition.

8 Claims, No Drawings

SOLVENT EXTRACTION PROCESS

This is a continuation of pending application Ser. No. 07/377,648, filed Jul. 10, 1989 now abandoned .

BACKGROUND OF THE INVENTION

1. Field of the Invention

This invention relates to a an improvement in the process for producing a polymer-drug microcapsule pharmaceutical composition wherein the composition comprises a core containing at least one water soluble, hormonally active polypeptide and, optionally, a polymer hydrolysis modifying agent encapsulated in a bioderodable or biodegradable, biocompatible (co)-polymer matrix. The improvement comprises a process for extracting volatile solvents entrained in the polymer-drug microcapsule pharmaceutical composition comprising the steps of (1) contacting the polymer-drug microcapsule pharmaceutical composition with a dense, that is, pressurized, gas and (2) then removing the dense gas, and the volatile solvents therein which have been extracted, from the polymer-drug microcapsule composition.

2. Description of Related References

Kent et al., U.S. Pat. No. 4,675,189 issued Jun. 23, 1987, discloses novel sustained release microcapsule compositions comprising water-soluble, hormonally-active polypeptides and, optionally, a polymer hydrolysis modifying agent, encapsulated in a biocompatible, biodegradable polymer.

More particularly, the patent covers a pharmaceutical composition designed for sustained release over a period of at least 1 month of a luteinizing hormone-releasing hormone (LHRH) analog, prepared in microcapsule form, comprising at least one LHRH analog or pharmaceutically acceptable salt thereof in an amount between about 0.01 and 40.0 wt. %, and a poly(lactide-co-glycolide) polymer (PLGA) having a lactic acid:-glycolic acid molar ratio of 75:25 to 40:60, the polymer being present in an amount of between about 99.99 and 60.0 wt. %.

The patented pharmaceutical composition contains as the polypeptide component preferably those nona- and deca-peptides that are LHRH analogs and that are disclosed in U.S. Pat. No. 4,234,571.

The patented pharmaceutical composition designed for sustained release of a therapeutically effective amount of polypeptide over an extended period of time comprising the LHRH analog and poly(lactide-co-glycolide) polymer was prepared in microcapsule form according to the method disclosed in Boswell et al., U.S. Pat. No. 3,773,919 issued Nov. 20, 1973.

In brief, the procedure for preparing the patented pharmaceutical composition designed for sustanied release of a hormonally active polypeptide, particularly a LHRH analog, in microcapsule form involves dissolving the polymer in a halogenated hydrocarbon solvent, dispersing an aqueous polypeptide-containing solution in this polymer-solvent solution, and adding some agent which is soluble in the halogenated hydrocarbon solvent but is a non-solvent for the encapsulating excipient. The addition of the non-solvent, called a coacervation agent, causes the polymeric excipient to precipitate out of the halogenated hydrocarbon solvent onto the dispersed polypeptide-containing water droplets, thereby encapsulating the polypeptide. For example, a poly(lactide-co-glycolide) polymer is dissolved in methylene chloride. An aqueous solution of polypeptide is then added with rapid stirring to the solvent-polymer solution forming a water-in-oil emulsion. A second solvent-miscible material such as silicone oil is added with slow stirring to cause the polymeric excipient to precipitate out of the methylene chloride and collect on the water-solvent interface which coats the dispersed water droplets to give microcapsules.

After being formed, the microcapsules are washed and hardened with a suitable organic solvent, washed with water, washed with an aqueous non-ionic surfactant solution, and then dried at room temperature under vacuum. The resulting microcapsules may range in diameter from about 1 to 500 microns, preferably from about 5 to about 200 microns.

Although the pharmaceutical composition containing an LHRH analog, for example, nafarelin in the form of its acetate salt, and the poly(lactide-co-glycolide) polymer in microcapsule form is suitable for its intended pharmaceutical use in treating human patients, the product tends to contain, or retain, some proportion of the solvents in the microcapsule product which are used in the manufacturing process. While the concentration of the residual solvents in the microcapsule product is not believed to render the resulting pharmaceutical composition unsuitable or unsafe for human use, it is preferred to reduce the concentration of the residual solvents in the microcapsule product, such as dichloromethane (methylene chloride) and heptane, in the pharmaceutical composition.

The residual methylene chloride and heptane, which are themselves volatile and readily evaporated in pure liquid form, appear to be entrapped, or entrained, within the spherical polymeric particles of the microcapsule product and thus rendered effectively non-volatile. Exposure of the product to reduced pressure (vacuum), for example, does not result in significant reduction in the levels of either solvent. Because these solvent residues, in particular the dichloromethane residue, are pharmaceutically undesirable, there is a need for a process or method to eliminate or to substantially reduce the amounts of such residual solvents in the microcapsular pharmaceutical composition containing a LHRH analog in combination with a poly(lactide-co-glycolide) polymer while leaving the product otherwise intact.

The use of dense gases and other forms thereof such as supercritical fluids has been known and reported in the purification of polymers by extraction of residual monomer and catalyst and water (Ger. Pat. Pubn. DE 3323940); the extraction of caffeine in the production of caffeine-free coffee extract (U.S. Pat. No. 3,843,824); the purification of hop extract, produced by extracting a hop extract produced by extraction of hops with a liquid organic solvent and contaminated with solvent residue, by extracting with supercritical carbon dioxide (AU Pat. Pubn. 8286745 having priority on Ger. Pat. Appln. DE 3131428); the extraction of an organic material from a solid by the solvent, namely $CO_2$ gas of supercritical condition, the pressure of the supercritical organic solvent being controlled with variation; and purifying maleic anhydride copolymer with olefins or vinyl aromatics by extraction with gas under supercritical conditions to remove hazardous compounds (Ger. Pat. Pubn. 0258416 having priority on Ger. Pat Appln. DD 300648).

SUMMARY OF THE INVENTION

This invention is a process for the extraction of volatile solvents entrained in a polymer-based pharmaceutical composition in microcapsule form wherein the composition comprises at least one hormonally-active water-soluble polypeptide in a therapeutically effective amount encapsulated in a biocompatible, bioerodable encapsulating polymer, which process comprises the steps of contacting the composition with a stream of dense gas and then removing the dense gas, and volatile solvents contained (that is, dissolved) therein, from the composition.

DETAILED DESCRIPTION OF THE INVENTION

This invention is, in the process for producing a polymer-drug microcapsule pharmaceutical composition comprising the steps of providing the polymer matrix, dissolving the polymer matrix in a halogenated hydrocarbon solvent, dispersing the polypeptide in the polymer-solvent solution, adding an agent which is soluble in the halogenated hydrocarbon solvent but is a non-solvent for the polymer so as to cause the polymer to precipitate out of the halogenated hydrocarbon solvent onto the dispersed polypeptide droplets, thereby encapsulating the polypeptide, washing the microcapsules, hardening the microcapsules, and then drying the microcapsules, the improvement comprising contacting the microcapsules with a dense gas for a time and at a pressure and temperature sufficient to swell the polymer matrix to an extent sufficient to extract from the microcapsules residual volatile solvents contained in the microcapsules and removing the dense gas and volatile solvents contained therein.

Hormonally active polypeptides are those polypeptides which have a specific regulatory effect on the activity of a certain body organ. Generally, they are secreted by an endocrine gland. Some peptides not secreted by an endocrine gland, however, exhibit a specific regulatory effect on a body organ and therefore are also classified as hormonally active compounds. Synthetically produced analogs of naturally occurring hormonally active polypeptides are to be considered as falling within the scope of this definition.

Pharmaceutically acceptable salts of the naturally occurring hormones and their synthetic analogs which retain the same type of activity as their parent also are to be considered within the scope of this invention.

Preferably, the polypeptide used in the composition subjected to the process according to this invention is an LHRH-active polypeptide, including LHRH itself and synthetic analogs thereof and pharmaceutically acceptable salts thereof, which act on the anterior pituitary gland to effect the release of hormones which affect the activity of reproductive organs. For purposes of this application, the expression "LHRH analog" is meant to encompass LHRH itself as well as the synthetic analogs thereof and pharmaceutically acceptable salts thereof.

LHRH analogs include compounds having agonist or antagonist effects. Representative LHRH agonists include, but are not limited to, those compounds that are disclosed in Nestor et al., U.S. Pat. No. 4,234,571 (Nov. 18, 1980). Representative LHRH antagonists include, but are not limited to, those compounds disclosed in Nestor et al., U.S. Pat. No. 4,801,577 (Jan. 31, 1989).

Other representative LHRH analogs include those nona- and decapeptides having LHRH agonist or antagonist thereof, in the following U.S. Pat. Nos. 3,813,382; 3,843,065; 3,849,389; 3,855,199; 3,886,135; 3,890,437; 3,892,723; 3,896,104; 3,901,872; 3,914,412; 3,915,947; 3,929,759; 3,937,695; 3,953,416; 3,974,135; 4,010,125; 4,018,914; 4,022,759; 4,022,760; 4,022,761; 4,024,248; 4,034,082; 4,072,668; 4,075,189; 4,075,192; 4,086,219; 4,101,538; 4,124,577; 4,124,578; 4,143,133; 4,253,997; 4,292,313; and 4,341,767.

The LHRH agonist compounds of greatest interest, and thus more preferred, herein are those polypeptide compounds that are the subject of U.S. Pat. No. 4,234,571 (Nov. 18, 1980), including their pharmaceutically acceptable salts. The disclosure of this patent is incorporated herein by reference. These polypeptides are nonapeptides and decapeptides represented by the formula:

(pyro)Glu-His-V-Ser-W-X-Y-Arg-Pro-Z (I)

and the pharmaceutically acceptable salts thereof wherein

V is

Trp (tryptophyl), Phe (phenylalanyl), or Nal (3-(1-naphthyl)-L-alanyl)

W is

Tyr (tyrosyl), Phe, or 3-(1-pentafluorophenyl)-L-alanyl;

X is a D-amino acid residue

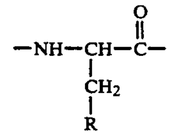

wherein R is (a) a carbocyclic aryl-containing radical selected group consisting of naphthyl, anthryl, fluorenyl, phenanthryl, biphenyl, benzhydryl and phenyl substituted with three or more straight chain lower alkyl groups; or (b) a saturated carbocyclic radiacal selected from the group consisting of cyclohexyl substituted with three or more straight chain lower alkyl groups. perhydronapthyl, perhydro-2,2-diphenylmethyl and adamantyl;

Y is leucyl, isoleucyl, nor-leucyl or N-methyl-leucyl; and

Z is glycinamide or —NH—$R^1$ wherein $R_1$ is lower alkyl, cycloalkyl, fluoro lower alkyl or

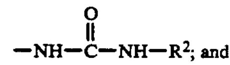

$R_2$ is hydrogen or lower alkyl.

Most preferred LH-RH agonists are those having formula (I) above wherein X is 3-(2-naphenylalanyl-D-alanyl or 3-(2,4,6-trimethylphenyl)-D-alanyl; Z is glycinamine; V is tryptophyl or phenylalanyl; W is tyrosyl and Y is leucyl or N-methylleucyl.

Especially preferred among the LHRH agonists, for use in the process according to this invention, is a polypeptide represented by the formula:

(pyro)Glu-His-Trp-Ser-$NH_2$ (nafarelin acetate)

The LHRH antagonist compounds of greatest interest, and thus, more preferred, herein are those polypeptide compounds that are the subject of U.S. Pat. No. 4,801,577, Jan. 31, 1989. These polypeptides are nonapeptides and decapeptides represented by the formula:

A-B-C-Ser-D-E-F-G-Pro-J (II)

or a pharmaceutically acceptable salt thereof, wherein:

A is an amino acyl residue selected from the group consisting of either the D- or the L- isomer of: N-Ac-D,L-$\Delta^{3,4}$-prolyl, N-Ac-D,L-prolyl, N-Ac-D,L-phenylalanyl, N-Ac-D,L-p-chlorophenylalanyl, N-Ac-D,L,-p-fluorophenylalanyl, N-Ac-3-(1-naphthyl)-D,L-alanyl, N-Ac-3-(2-naphthyl)-D,L-alanyl, and N-Ac-3-(2,4,6-trimethylphenyl)-D,L-alanyl;

B is an amino acyl residue selected from the group consisting of D-phenylalanyl, D-p-chlorophenylalanyl, D-p-fluorophenylalanyl, D-p-nitrophenylalanyl, 2,2-diphenylglycyl, D-α-methyl-p-chlorophenylalanyl and 3-(2-naphthyl)-D-alanyl;

C is an amino acyl residue selected from the group consisting of D-tryptophanyl, D-phenylalanyl, 3-(3-pyridyl)-D-alanyl, and 3-(2-naphthyl)-D-alanyl;

D is an amino acyl residue selected from the group consisting of L-phenylalanyl, L-tyrosyl, and 3-(3-pyridyl)-alanyl, arginyl, or G;

E is 3-(2-naphthyl)-D-alanyl, 3-(3-pyridyl)-D-alanyl, D-tyrosyl, D-tryptophanyl, D-nicotinyl-lysyl, pyridylacetyl-lysyl, D-Glu(AA) or G;

F is an amino acyl residue selected from the group consisting of L-leucyl, L-norleucyl, L-phenylalanyl, L-tryptophanyl, and 3-(2-naphthyl)-L-alanyl;

G is an amino acyl residue selected from the group consisting of the radicals represented by the following structural formulas:

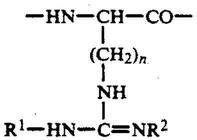

wherein n is 1 to 5;

$R^1$ is alkyl of 1 to 6 carbon atoms or fluoroalkyl;

$R^2$ is hydrogen or $R^1$; or $R^1$—HN—C═$NR^2$ is a ring represented by the following structural formulas:

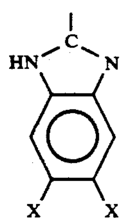

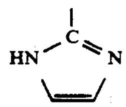

-continued

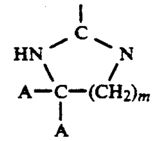

wherein m is 1 to 4; A is hydrogen or alkyl of 1 to 6 carbon atoms; and X is halo or A; and (b)

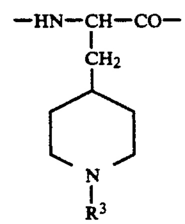

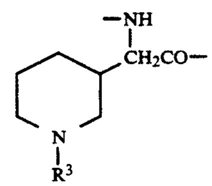

wherein $R^3$ is hydrogen, alkyl of 1 to 6 carbon atoms, phenyl or phenyl loweralkyl; and J is D-alaninamide; D-leucinamide; glycinamide; or —$NHR^4$ wherein $R^4$ is lower alkyl or $NHCONH_2$.

Still more preferred LHRH antagonists are those wherein A is N-Ac-D-Nal(2) or N-Ac-D-pCl-Phe; B is D-pF-Phe or D-pCl-Phe; C is D-Trp, D-Nal(2) or Pal(3); D is Pal(3), Tyr, Arg, Deh, Mbh, Bth, or Pha; E is D-Trp, D-Tyr, D-Nal(2), D-Pal(3), D-Deh, D-Mbh, D-Pha or D-Bth; F is Leu or Phe; G is Deh, Bth, Mbh, or Pha; and J is D-$AlaNH_2$ or $GlyNH_2$.

Most preferred LHRH antagonists are those wherein:

A is N-Ac-D-Nal(2);

B is D-pCl-Phe;

C is D-Trp or D-Pal(3);

D is Tyr, Arg, Deh, Mbh, Bth or Pha;

E is D-Trp, D-Pal(3), D-Nal(2), D-Tyr, D-Deh, -Mbh, D-Bth or D-Pha;

F is Leu;

G is Deh, Mbh, Bth or Pha; and

J is D-$AlaNH_2$.

Especially preferred among said LHRH antagonist are polypeptides represented by the formula:

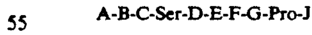

wherein A in N-Ac-D-Nal(2), B is D-pCl-Phe, C is D-Pal(3), D is Tyr, E is selected from D-Deh and D-Pal(3), F is Leu, G is Deh, and J is Ala-$NH_2$.

The compositions are formulated to contain the polypeptide in an amount which may vary between 0.01 and 40.0, preferably between 0.1 and 10.0, weight percent of the polymer used for encapsulation. The amount of peptide used in a particular formulation depends not only on daily dose but also on the number of days that dose level is to be maintained and, further, on the degradation and/or erosion characteristics of the encapsulating polymer.

A number of polymers have been developed which meet the criteria of being biocompatible and bioerodable and/or biodegradable. Examples of suitable polymers are disclosed in Kent et al., U.S. Pat. No. 4,675,189.

Preferably, the polymer matrix used in the composition subjected to the process according to this invention is a polymer prepared from lactic acid as the sole monomer or as the principal monomer and glycolic acid as the comonomer, the latter copolymer being referred to as "poly(lactide-co-glycolide) copolymers" or "poly(-lactic-co-glycolic acid polymers" (PLGA).

The combinations of preferred monomer and comonomer which can be prepared are numerous but the most effective polymer matrices are those polymers prepared from lactic acid alone or lactic acid and glycolic acid wherein the glycolic acid is present as a comonomer in a molar ratio of 100:0 to about 40:60 (lactic:glycolic). Most preferably there is used a poly(lactic-co-glycolic acid) copolymer (PLGA) having a molar ratio between 75:25 and 50:50.

Poly(lactic-co-glycolic acid) polymers preferably will range in molecular weight from about 20,000 to about 100,000, stated as average. The molecular weight of a particular polymer is independent of its monomeric makeup. Thus, polymers can be varied both as to their monomer composition as well as to their molecular weight and be within the scope and intent of the polymer used in the composition subjected to the process according to this invention.

The preparation of PLGA polymer matrices and of polymer-drug microcapsules is disclosed in Kent et al., U.S. Pat. No. 4,675,189 and Boswell et al., U.S. Pat. No. 3,773,919, the disclosure of which is incorporated herein by reference.

By way of practical exemplary description, the process of producing the PLGA-drug microcapsules involves dissolving a PLGA polymer matrix in methylene chloride. Polypeptide is then added with rapid stirring to the solvent-polymer solution forming an emulsion. A second solvent-miscible material such as silicone oil is added with slow stirring to cause the polymer matrix material to precipitate out of the methylene chloride and collect on the polypeptide particle interface which coats the dispersed polypeptide particles to give microcapsules.

Halogenated organic solvents which may be used in the preparation of the PLGA polymer matrices are the $C_1$ to $C_4$ halogenated hydrocarbons such as, for example, methylene chloride, ethylene dichloride, ethylene chloride, 2,2,2-trichloroethane and the like.

Coacervation agents (that is, non-solvents) may be any solvent miscible polymeric, mineral oil or vegetable oil compounds which are non-solvents for the encapsulating polymers. There may be used, for example, silicone oil, peanut oil, soybean oil, corn oil, cotton seed oil, coconut oil, linseed oil, and the like.

After being formed, the microcapsules are washed and hardened with a suitable organic solvent, washed with water, washed with an aqueous non-ionic surfactant solution, and then dried at room temperature under reduced pressure (vacuum).

Microcapsules may range in diameter from about 1 to about 500 microns, depending upon the techniques employed. Preferably, the microcapsule diameter will be between about 5 and 200 microns.

As mentioned above, the microcapsule product so produced tends to contain entrained therein some portion of the solvents used in the manufacturing process, namely dichloromethane and heptane, the concentration of which is not significantly reduced upon exposure to reduced pressure (i.e. vacuum) for the ordinary time in the manufacturing process, e.g. several tens of hours to several days.

One possible factor that may contribute to retention of these solvents within the microcapsules may be a very slow rate of diffusion of the solvents through the polymer matrix. The rate of diffusion of small molecules through a polymer can be increased by heating the material to temperatures above its glass transition temperature ($T_g$), or by expanding ("swelling") the polymer matrix by the introduction of solvents which dissolve in the solid material and thus increase its volume.

The physical form, chemical composition, and intended use of the PLGA-LHRH analog microcapsule product limit the means available for removal of the solvents. For example, the product cannot be heated significantly in order to facilitate separation of the entrained solvents without softening the polymer, which results in individual particles adhering to each other (agglomeration). Agglomeration of the particles is undesirable since it interferes with the injectability of the microcapsules. In addition, heating might accelerate degradation of the drug contained within the microcapsules and might adversely affect the polymer itself.

Selection of conditions for swelling the polymer to increase the rate of diffusion of the entrapped solvents through the polymer is subject to several constraints. A solvent selected for this purpose must interact strongly enough to penetrate and solvate the interior of each particle. However, the relatively low molecular weight of the PLGA polymer material leads to actual solubility of the polymer in some solvents, thereby destroying the product. A solvent selected for the purpose of swelling the polymer must posses low toxicity since a residue of such solvent might be present after removal of the undesired processing solvents and drying of the swelled product. The degree of swelling must be controlled, since excessive swelling leads to softening of the material and can result in agglomeration or coalescence of the particles. The process must also leave the polypeptide, for example, an LHRH analog such as nafarelin acetate, intact and unextracted, and must not alter polypeptide distribution within the polymer matrix by, for example, dissolution of the individual nafarelin acetate particles. Finally, the selected swelling agent must not react chemically with any component of the product and must not change the medically useful properties of the product.

Among the methods considered for investigations to remove the residual solvents from PLGA-drug, particularly PLGA-LHRH analog and more particularly PLGA-nafarelin acetate, microcapsules was treatment of the microcapsules with supercritical $CO_2$ to extract the residual solvents. However, such treatment resulted in varying degrees of agglomeration and fusion of the microspheres (microcapsules) to form a useless mass having the appearance of a "golf ball".

This invention is the unexpected and surprising discovery that pressurized gaseous $CO_2$ is capable of swelling the polymer matrix of the PLGA-LHRH analog, namely, PLGA-nafarelin acetate, product thereby allowing the trapped solvent residues to diffuse to the surface of the particles and to evaporate, and that the degree of swelling and efficiency of solvent extraction can be controlled by variation in the applied gas pressure. Further, limits of gas pressure which allow the removal of residual dichloromethane without excessive swelling and consequent agglomeration have been determined.

As the dense gas, there may be used pressurized gaseous $CO_2$ (carbon dioxide) and also mixtures of other gases or liquids with pressurized gaseous $CO_2$ such as, for example, gaseous or liquid pressurized $C_3H_8$ (propane), $C_5H_{12}$ (pentane) or $C_7H_{16}$ (heptane) in combination with pressurized gaseous $CO_2$. Especially preferred is the combination (or admixture) of pressurized gaseous $CO_2$ with liquid pressurized propane, e.g. propane, about 110 psig plus $CO_2$ to 400 psig.

The lower pressure limit for effective mobilization of solvents by gaseous $CO_2$ or mixtures thereof with other gases, especially mixtures of $CO_2$ with $C_3H_8$ thereof at ambient temperature within the microcapsule product polymer (PLGA) matrix has been observed to be about about 110 psig of $CO_2$ pressure alone, while agglomeration of the individual particles has been observed to become significant at pressures above about 250 psi of $CO_2$ pressure alone. The addition of $C_3H_8$ has been found to extend the useful partial pressure of $CO_2$ upward. The microcapsules are contacted with the pressurized gas for about 5 minutes to 150 hours.

The following examples, including tables and figures herein described, are illustrative of but a few embodiments of the invention and are not to be construed as limiting in scope. All parts and percentages are by weight and all temperatures are in degrees Celsius unless otherwise indicated.

EXAMPLE A

This example describes a typical procedure for preparing a microcapsule composition wherein the polypeptide is (pyro)Glu-His-Trp-Ser-3-(2-naphthyl)-D-Ala-Leu-Arg-Pro-Gly-$NH_2$, (D-Nal$(2)^6$LH-RH) present in an amount of 1.4% by weight, no polymer hydrolysis modifying agent is present, and the excipient is a 50:50 molar ratio poly(lactide-co-glyclolide)copolymer having an inherent viscocity in hexafluoroisopropanol of 0.38 dl/g at 30° C.

Excipient (PLGA), 4 g, was dissolved in 196 g of methylene chloride. This solution was placed in a 300 ml resin kettle equipped with a true-bore stirrer having a 2.5 inch Teflon turbine impeller driven by a Fisher "Stedi-Speed" motor. In a 1-dram glass vial was dissolved 0.0571 g of polypeptide in 1.34 g of deionized water.

This solution was added to the resin kettle. During this addition, the dilute polymer solution was stirred at 3200 RPM to form a water-in-oil emulsion. With continued stirring at that rate, 80 ml of silicone oil was added at the rate of 4.0 ml/min by means of a peristaltic pump. The silicone oil caused the polymer to phase separate, and deposit as droplets of solvent-swollen polymer onto the surface of the water-polypeptide microdroplets. These solvents-swollen polymer droplets then coalesced to form a continuous film around the water-polypeptide microdroplets. The microcapsules were then hardened by pouring the contents of the resin kettle into a beaker containing 2000 ml of heptane. This mixture was stirred at 1000 RPM for 30 minutes with a stainless-steel impeller. The heptane-methylene chloride-silicone oil solution was removed by filtering the solution, employing a Buchner funnel and Whatman No. 41 filter paper. The microcapsules were then washed repeatedly with 100 ml aliquots of heptane to insure complete removal of the silicone oil. The microcapsules were then washed with deionized water followed by a wash with a 1% aqueous solution of Tween 20 . and dried at room temperature under vacuum. Microcapsules obtained from this preparation were determined to have diameters ranging in size from 10 to 40 microns.

By modification of parameters, conditions and materials, numerous variations of the above procedure will be apparent to those skilled in the pertinent art.

EXAMPLE B

This example illustrates the unsuccessful efforts to further purify PLGA-nafarelin acetate microcapsules by employing conventional supercritical $CO_2$ extraction technology. The general technique is described in this section: III.2C Preparative extraction, Pages 44–46, of "Dense Gases for Extraction and Refining" Sthal, Quirin and Gerard, 1986, Springer-Verlag, Berlin.

Three experiments were performed in which supercritical carbon dioxide (supercritical $CO_2$) was contacted with samples of PLGA microcapsules.

B.1 A sample of 3.8 g of PLGA microcapsules was loaded into a conventional tubular extractor. Employing conventional techniques, carbon dioxide at 25–27 degrees C. and 4000 psi was pumped through the tubular extractor containing the sample at 4–5 g/min for 2.0 hours. The sample fused into a solid pellet.

B.2 A sample of 0.3 g of PLGA microcapsules was loaded into a glass high pressure reaction flask having a gas/liquid inlet and the flask was sealed. Carbon dioxide (1,000 psig) was slowly introduced into the flask to maintain the temperature below ambient temperature. The microcapsule sample immediately agglomerated when contacted with the carbon dioxide.

B.3 This experiment is a modification of Example B.2 above. A sample of 0.3 g of PLGA-nafarelin acetate microcapsules was loaded into a glass high pressure reaction flask having a gas/liquid inlet and the flask was sealed. The flask was filled with liquid carbon dioxide. The flask was held at room temperature and was occasionally shaken by hand for a period of 1 hour. Then, the carbon dioxide was drained. This procedure was repeated twice. The microcapsule sample agglomerated under these experimental conditions.

Although the application of conventional supercritical $CO_2$ extraction technology effected agglomeration and was thus unsatisfactory because such treatment destroyed product integrity, analysis (conventional gas chromatography) of the residues showed that methylene chloride concentration in the resulting product mass was below detectable limits and that alkane concentration ($C_7H_{16}$ and $C_5H_{12}$) was less than 0.5%. Typical control concentrations of methylene chloride and heptane in the PLGA-nafarelin acetate microcapsules are 0.16% and 11.3%, respectively.

EXAMPLE 1

A sample of the product (PLGA-nafarelin acetate microcapsules according to Example A) was placed within a steel pressure vessel and, by means of appropriate control apparatus, was exposed to a slowly flowing stream of carbon dioxide gas at pressures which varied smoothly and in a cyclic fashion from vacuum (1 mm Hg) to a higher pressure (about 250 psi). Reduction of pressure from the maximum value was carried out slowly in order to prevent disruption of the product particles as a result of internal pressure. After sixty-five repetitions of the pressure cycle, the sample was removed and assayed for its solvent content and for its performance in an in vitro nafarelin acetate release test, which predicts the pharmaceutical performance of the material.

The solvent content of the unprocessed sample was 6.0% heptane and 400 ppm (parts per million) dichloromethane, while the sample subjected to gas extraction contained 5.1% heptane and less than 80 ppm dichloromethane. 80 ppm is the detection limit of the analysis procedure for dichloromethane. The in vitro drug release assay showed that the processing of the sample had not affected its pharmaceutical performance characteristics, and microscopic examination of the product before and after extraction showed no significant changes in particle shape or size.

EXAMPLE 2

A second sample of the product was extracted in a similar fashion to that described in Example 1, except that the gas pressure was varied between limits of 160 and 230 psi. This sample initially contained 9.9% heptane and 0.66% (6600 ppm) dichloromethane. After the treatment with pressurized carbon dioxide, the heptane content was reduced to 8.6%, and the dichloromethane level was less than 80 ppm, demonstrating that the application of vacuum during the process is not necessary.

EXAMPLE 3

A third sample was placed in a 4.5×250 mm stainless steel tube and was exposed to a slowly flowing stream of carbon dioxide gas at a variety of pressures. The exhausted gas, after expanding to atmospheric pressure, was passed through the measurement cell of an infrared spectrophotometer. The infrared absorption spectrum of the exhaust gas from the apparatus, flowing at a constant rate, was recorded periodically as the gas pressure to which the sample was subjected was increased. This technique allowed the direct observation of the extracted solvents in the exhaust stream by means of their characteristic molecular vibrational absorptions.

At atmospheric pressure, neither solvent present in the sample was detected in the exhaust gas. When the carbon dioxide pressure impinging on the sample reached approximately 150 psi, the characteristic absorption spectrum of dichloromethane became apparent in the exhaust gas, indicating the onset of its extraction from the product. As the pressure on the sample was increased further, the intensity of this spectrum increased and the spectrum of heptane appeared, indicating that both solvents were being removed from the sample and that the rate of removal was a function of the applied gas pressure.

In a separate experiment using the same apparatus, the intensity of the spectra due to the two solvents was recorded and plotted as a function of extraction time at a constant carbon dioxide pressure of 230 psi. The concentration of dichloromethane in the exhaust stream declined rapidly as the extraction progressed, and the spectrum ultimately became undetectable. The absorptions due to heptane decreased more slowly. When the product sample was subsequently analysed for residual solvent content, the dichloromethane content was again found to have been reduced to undetectable levels, and the heptane level had been slightly lowered.

EXAMPLE 4

This example illustrates the effect of the use of pressurized hydrocarbon(s) in combination with dense gaseous $CO_2$ wherein the liquid pressurized hydrocarbon is used to swell the polymer matrix. The samples were contacted with the dense gas set forth in each experiment employing conventional technology.

The "sight-cell" used in the following experiment was a Transparent Liquid Level Gage #1 available from Inferno Manufacturing Support Corporation, Shreve Port, La. The gage was filled at each end with valves, a pressure gage, fill lines, etc. It was loaded with samples by unscrewing the fittings from one end, filling with sample and replacing the fitting. The use of cotton plugs in each end kept the sample suspended in liquified gases in the visible portion. Internal working volume was 50 ml.

4.1 A sample of 0.4 g of PLGA microcapsules was loaded in a glass and stainless steel sight cell. About 50 ml of liquid propane LP was introduced (75% full sight cell) at RT and at its vapor pressure of 110 psig. Cell was shaken occasionally over a 1 hr period, then allowed to stand overnight. Drain out LP in morning and recharge cell with fresh LP. Shake cell occasionally during next 8 hr period. Let the cell again stand overnight. Repeat drain, fill and shaking procedure once more. Total elapsed time of powder in LP was 42 hr. The microcapsules became a free-flowing slurry when suspended in LP. After depressurizing and unloading the cell, the powder appeared same as before, perhaps less sticky and more free-flowing. About 0.05% of $CH_2Cl_2$ and 9% of heptane was detected.

4.2 A sample of about 0.8 g of PLGA microcapsules was leaded into sight cell. About 50 ml of LP introduced stepwise. Cell shaken after each carbon dioxide addition to observe stickiness of supended powder. Steps correspond to total cell pressures of: 110 (LP only); with added $CO_2$, total cell pressures are 160, 180, 200, 250, 300, and 400 psig. Powder became progressively stickier until it was all adhering in clumps to inside cell surfaces at 400 psig. Let stand overnight in mixed liquid phase (19.5 hrs.), drain and depressurized. The microcapsules lightly fused into pliable, open structured lumps. No $CH_2Cl_2$ was detected and 1.0% of heptane was detected.

4.3 A sample of 1.1 g of PLGA microcapsules was loosely packed in transparent 1.0 cm ID plastic tube mounted inside the sight cell. Carbon dioxide at 18°-20° C. and 200 psig (constant) was passed through the tube for 24 hr at a rate of 20-30 ml/min (STP). The column of microcapsules (powder) had solidified but was easily reground in the mortar and pestle to its original consistency. No residual $CH_2Cl_2$ was detected and 5.8% of heptane was detected.

4.4 A samnle of 0.5 g of PLGA microcapsules was ground to a fine powder and loaded into a sight cell with 25 ml of heptane and the cell was sealed. Carbon dioxide at 18°-20° C. was slowly introduced into the cell until total pressure was 420 psig. The cell was shaken occasionally, then allowed to stand overnight and finally heptane and carbon dioxide was drained. The total time under carbon dioxide pressue was about 18 hr. Clumped powder samples were removed. No $CH_2Cl_2$ was detected and 4.3% of heptane was detected.

4.5 The procedure described in example 4.4 above was repeated except that 25 ml of pentane was substituted for heptane and the carbon dioxide pressure was 400 psig and the total time under carbon dioxide pressure was about 4 hrs. Clumped powder samples were removed.

About 0.125% of $CH_2Cl_2$ and 0.85% of heptane was detected. Thus, insufficient $CH_2Cl_2$ was removed.

4.6 A sample of 4.28 g of finely powdered PLGA microcapsules was placed in a 60 ml fritted glass filter funnel (medium porosity 4.0 cm diameter) to a depth of 0.6 cm. The funnel was loaded upright in a conventional pressure vessel. The funnel stem was attached to a carbon dioxide inlet tube. The vessel was sealed and then pressurized with carbon dioxide to 200 psig and carbon dioxide began flowing upward through the funnel. The vessel was maintained at 200 psig of carbon dioxide introduced at a flow rate of 0.3 cfm (STP) (measured with a rotameter) for 24 hrs at a temperature of 19°-20° C. Then the vessel was vented and the sample was removed as a solid disc. No. $CH_2Cl_2$ was detected but about 7.4% of heptane was detected.

The results of Examples B.1, B.2, 4.1, 4.2, 4.3, 4.5 and 4.6 are summarized in Table I. Table I shows that the process of Example 4.2 is especially advantageous and, thus, preferred.

TABLE I

| EX. NO. | DENSE GAS(ES) | $MeCl_2$ | HEPTANE | COMMENTS |
|---|---|---|---|---|
| B.1 | $CO_2$, 4,000 psig | | | Destroyed microspheres |
| B.2 | Liquid $CO_2$ (<1,000 psig) | | | Destroyed microspheres |
| 4.1 | Propane, 100 psig | 0.05 | 9 | No extraction |
| 4.2 | Propane, 110 psig plus $CO_2$ to 400 psig | N.D.* | 1.0 | Propane fluidization allows better heptane extraction |
| 4.3 | $CO_2$, 200 psig Microspheres arranged as in a packaged tubular column | N.D.* | 5.8 | Microspheres compaction hinders heptane removal |
| 4.4 | $CO_2$ at 200 psig plus heptane | N.D.* | 4.3 | Removes methylene chloride, but not as effectine as propane in removing residual hydrocarbons |
| 4.5 | $CO_2$ at 200 psig plus pentene to 400 psig | 0.125 | 0.85 | Insufficient methylene chloride removal |
| 4.6 | $CO_2$, 200 psig Microspheres arranged in a thin bed | N.D.* | 7.4 | $CO_2$ insufficient to remove enough heptane residue |

*Not detectable

What is claimed is:

1. A process for producing a polymer-drug microcapsule pharmaceutical composition, wherein the drug is at least one hormonally-active water-soluble polypeptide in a therapeutically effective amount, comprising the steps of (a) providing the polymer matrix, (b) dissolving the polymer matrix in a halogenated hydrocarbon solvent, (c) dispersing the polypeptide in the polymer-solvent solution, (d) adding a coacervation agent which is soluble in the halogenated hydrocarbon solvent but is a non-solvent for the polymer so as to cause the polymer to precipitate out of the halogenated hydrocarbon solvent onto the dispersed polypeptide droplets, thereby encapsulating the polypeptide, (e) washing the microcapsules, (f) hardening the microcapsules with an organic solvent and then (g) drying the microcapsules, (h) contacting the microcapsules with a gas selected from carbon dioxide at a pressure of from about 150 to about 250 psig and mixtures of carbon dioxide with $C_3H_8$, $C_5H_{12}$, or $C_7H_{15}$ at a total pressure of from about 110 psig to about 400 psig for a time sufficient to dissolve and thereby extract from the microcapsules residual volatile solvents contained in the microcapsules and then (i) removing the gas and volatile solvents contained therein.

2. A process according to claim 1 wherein the gas is a mixture of $C_3H_8$ and $CO_2$.

3. A process according to claim 2 wherein the propane is present at about 110 psig and the $CO_2$ is present at about 290 psig.

4. A process according to claim 1 wherein the gas is maintained at a constant pressure.

5. A process according to claim 1 wherein the period of contact of the microcapsules with the gas is from about 5 minutes to about 150 hours.

6. A process according to claim 1 wherein the polypeptide is a hormonally active polypeptide having LHRH-like activity selected from LHRH and synthetic analogs thereof and is present in the microcapsule composition in an amount of from about 0.01 to about 40.0 weight percent of the polymer used for encapsulation.

7. A process according to claim 1 wherein the polymer matrix is a poly(lactic-co-glycolic acid) copolymer (PLGA) having a lactic acid:glycolic acid monomer ratio of 100:0 to about 40:60 and having a molecular weight of from about 20,000 to about 100,000.

8. A process according to claim 1 wherein in step (c) the polypeptide is contained in aqueous solution.

* * * * *

UNITED STATES PATENT AND TRADEMARK OFFICE
CERTIFICATE OF CORRECTION

PATENT NO. : 5,232,707

DATED : August 3, 1993

INVENTOR(S) : David M. Lokensgard

It is certified that error appears in the above-identified patent and that said Letters Patent is hereby corrected as shown below:

Claim 1, at column 14, line 10 "$C_7H_{15}$" should read --$C_7H_{16}$--.

Signed and Sealed this

Fifth Day of April, 1994

Attest:

BRUCE LEHMAN

*Attesting Officer*

*Commissioner of Patents and Trademarks*